United States Patent
Leavens (10) Patent No.: US 9,744,346 B2
(45) Date of Patent: Aug. 29, 2017

(54) IMPLANTABLE STIMULATING ASSEMBLY ARRANGEMENTS

(71) Applicant: Cochlear Limited, Macquarie University, NSW (AU)

(72) Inventor: Jason Leavens, Bellevue Hill (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/799,769

(22) Filed: Jul. 15, 2015

(65) Prior Publication Data

US 2016/0015965 A1    Jan. 21, 2016

Related U.S. Application Data

(60) Provisional application No. 62/025,603, filed on Jul. 17, 2014.

(51) Int. Cl.
*A61N 1/05* (2006.01)

(52) U.S. Cl.
CPC .................... *A61N 1/0541* (2013.01)

(58) Field of Classification Search
CPC .... A61N 1/0541; A61N 1/36032; A61F 11/04
USPC .................................. 607/136–137
See application file for complete search history.

(56) References Cited

U.S. PATENT DOCUMENTS

| 4,819,647 | A | * | 4/1989 | Byers | ................... | A61N 1/0541 128/903 |
| 5,653,742 | A | | 8/1997 | Parker et al. | | |
| 6,119,044 | A | | 9/2000 | Kuzma | | |
| 6,125,302 | A | | 9/2000 | Kuzma | | |
| 7,367,992 | B2 | | 5/2006 | Dadd | | |
| 7,451,000 | B2 | | 11/2008 | Gibson et al. | | |
| 7,974,712 | B2 | | 7/2011 | Gibson et al. | | |
| 8,145,326 | B2 | | 3/2012 | Abbasi et al. | | |
| 8,311,649 | B2 | | 11/2012 | Frijns et al. | | |
| 8,473,075 | B2 | | 6/2013 | Gallegos et al. | | |
| 8,620,459 | B2 | | 12/2013 | Gibson et al. | | |
| 2002/0029074 | A1 | * | 3/2002 | Treaba | ................. | A61N 1/0541 607/137 |
| 2004/0225336 | A1 | * | 11/2004 | Milojevic | ............ | A61N 1/0541 607/57 |
| 2007/0088335 | A1 | | 4/2007 | Jolly | | |

(Continued)

FOREIGN PATENT DOCUMENTS

WO    2008/031144 A1    3/2008

OTHER PUBLICATIONS

International Search Report and Written Opinion in counterpart International Application No. PCT/IB2015/055360, mailed Nov. 19, 2015, 11 pages.

(Continued)

*Primary Examiner* — Paula J Stice
(74) *Attorney, Agent, or Firm* — Edell, Shapiro & Finnan, LLC (57) ABSTRACT

Embodiments presented herein are generally directed to a stimulating assembly of a cochlear implant that includes a perimodiolar flexure. The perimodiolar flexure is formed in a basal section of the stimulating assembly and has elastic properties and a shape so as to, after insertion into the cochlea, position the stimulating contacts disposed in the basal section of the stimulating assembly adjacent to a modiolar wall of the cochlea.

20 Claims, 11 Drawing Sheets

(56) References Cited

U.S. PATENT DOCUMENTS

| | | |
|---|---|---|
| 2008/0058914 A1 | 3/2008 | Abbasi et al. |
| 2011/0137393 A1 | 6/2011 | Pawsey et al. |
| 2012/0071957 A1 | 3/2012 | Carter |
| 2015/0119967 A1 | 4/2015 | Pawsey et al. |

OTHER PUBLICATIONS

"Circlip Electrode," An IP.com Prior Art Database Technical Disclosure, IPCOM000225812D, Mar. 7, 2013, 3 pages.

\* cited by examiner

IMPLANTABLE STIMULATING ASSEMBLY ARRANGEMENTS

CROSS-REFERENCE TO RELATED APPLICATIONS

The present application claims priority to U.S. Provisional Patent Application No. 62/025,603, filed on Jul. 17, 2014, the content of which is hereby incorporated by reference herein.

BACKGROUND

Field of the Invention

The present invention relates generally to an implantable stimulating assembly.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect of the invention, a stimulating assembly for insertion into a cochlea of a recipient through an opening in the cochlea is provided. The stimulating assembly comprises an elongate carrier member having a basal section configured to be implanted in a basal region of the recipient's cochlea, a plurality of stimulating contacts disposed along at least a first surface of the carrier member, wherein a subset of the stimulating contacts are disposed in the basal section, and a perimodiolar flexure formed in the basal section having elastic properties and a shape so as to, after insertion into the cochlea, position all of the stimulating contacts disposed in the basal section adjacent to a modiolar wall of the cochlea.

In another aspect of the invention, an apparatus is provided. The apparatus comprises an elongate carrier member having a proximal section and a distal section, and a plurality of stimulating contacts disposed in the carrier member. The carrier member comprises a pre-formed perimodiolar flexure forming a substantially continuous arcuate bend in the proximal section that a first surface of the proximal section includes a convex curve and a second opposing surface of the proximal section includes a concave curve.

In another aspect of the invention, a method for manufacturing an intra-cochlear stimulating assembly is provided. The method comprises forming a pre-curved superelastic shaping member so as to include a curled distal section and a continuous arcuate bend in a proximal section, assembling a plurality of stimulating contacts and lead wires in a straight configuration, temporarily straightening the pre-curved superelastic shaping member, positioning the superelastic shaping member adjacent to the stimulating contacts and lead wires within a molding die, and injecting a silicone or other polymer into the molding die to encapsulate the stimulating contacts, lead wires, and the superelastic shaping member, thereby forming a single assembly that is operable to substantially take the shape of the pre-curved superelastic shaping member.

BRIEF DESCRIPTION OF THE DRAWINGS

Embodiments of the present invention are described herein in conjunction with the accompanying drawings, in which.

DETAILED DESCRIPTION

Embodiments presented herein are generally directed to a stimulating assembly of a cochlear implant that includes a perimodiolar flexure. The perimodiolar flexure is formed in a basal section of the stimulating assembly and has elastic properties and a shape so as to, after insertion into the cochlea, position the stimulating contacts disposed in the basal section of the stimulating assembly adjacent to a modiolar wall of the cochlea.

Figure 1:
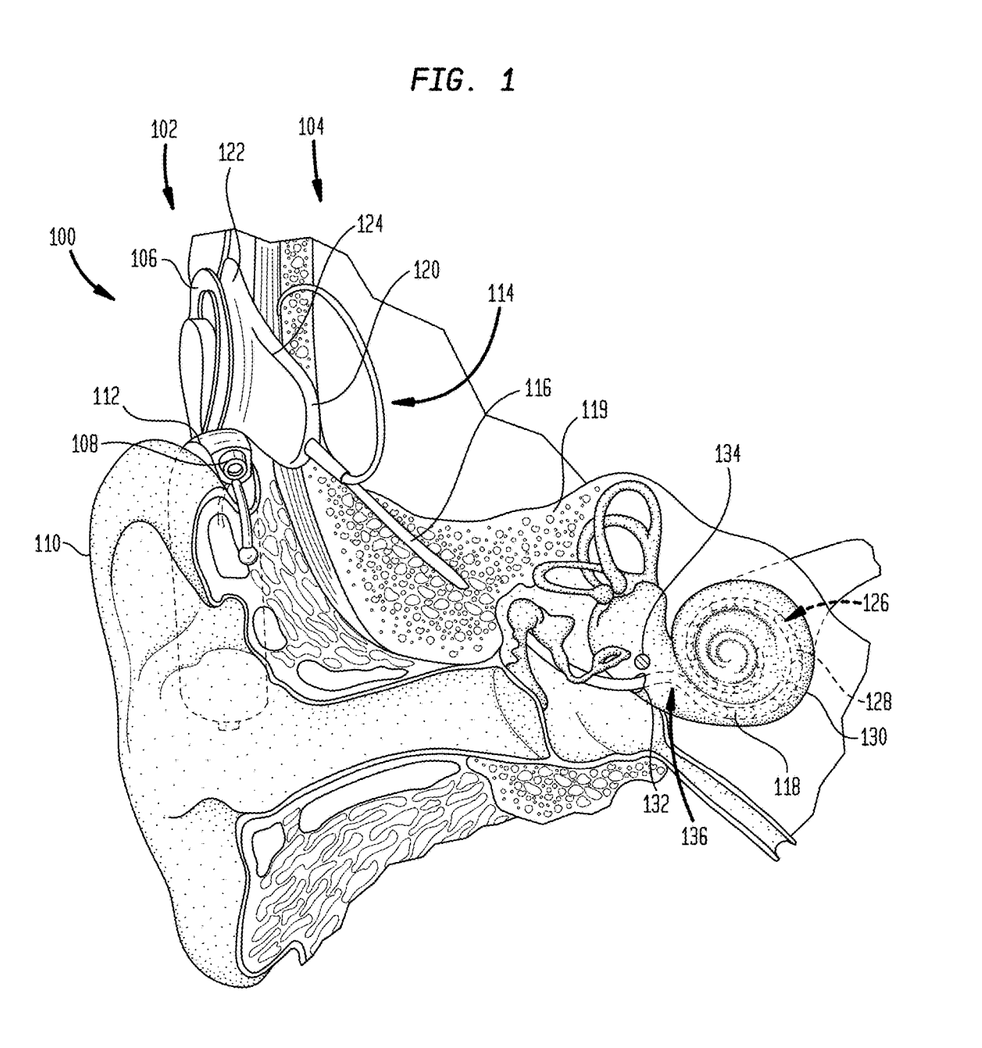
FIG. 1 is a schematic diagram of an implanted cochlear implant comprising a stimulating assembly having a perimodiolar flexure in accordance with embodiments presented herein.

FIG. 1 is perspective view of an exemplary cochlear implant 100 in accordance with embodiments presented herein. The cochlear implant 100 includes an external component 102 and an internal or implantable component 104. The external component 102 is directly or indirectly attached to the body of the recipient and typically comprises an external coil 106 and, generally, a magnet (not shown in FIG. 1) fixed relative to the external coil 106, one or more sound input elements 108 (e.g., microphones, telecoils, etc.) for detecting sound and a sound processing unit 112. The sound processing unit 112 may include, for example, a power source (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via a cable (not shown in FIG. 1).

FIG. 1 illustrates an example in which cochlear implant 100 includes an external component 102 with an external sound processor. It is to be appreciated that the use of an external component is merely illustrative and that the techniques presented herein may be used in arrangements having an implanted sound processor (e.g., totally implantable cochlear implants). It is also to be appreciated that the individual components referenced herein, e.g., sound input element 108 and the sound processor in sound processing unit 112, may be distributed across more than one tissue-stimulating prosthesis, e.g., two cochlear implants 100, and indeed across more than one type of device, e.g., cochlear implant 100 and a consumer electronic device or a remote control of the cochlear implant 100.

The implantable component 104 comprises an implant body 114, a lead region 116, and an elongate intra-cochlear stimulating assembly 118. The implant body 114 comprises a stimulator unit 120, an internal coil 122, and an internal receiver/transceiver unit 124, sometimes referred to herein as transceiver unit 124. The transceiver unit 124 is connected to the internal coil 122 and, generally, a magnet (not shown) fixed relative to the internal coil 122.

The magnets in the external component 102 and implantable component 104 facilitate the operational alignment of the external coil 106 with the internal coil 122. The operational alignment of the coils enables the internal coil 122 to transmit/receive power and data to/from the external coil 106. More specifically, in certain examples, external coil 106 transmits electrical signals (e.g., power and stimulation data) to internal coil 122 via a radio frequency (RF) link. Internal coil 122 is typically a wire antenna coil comprised of multiple turns of electrically insulated single-strand or multi-strand platinum or gold wire. The electrical insulation of internal coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to cochlear implant and FIG. 1 illustrates only one example arrangement.

Elongate stimulating assembly 118 is configured to be at least partially implanted in cochlea 130 and includes a plurality of intra-cochlear stimulating contacts 128. The stimulating contacts 128 collectively form a contact array 126 and may comprise electrical contacts and/or optical contacts.

Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120. As described further below, the stimulating assembly 118 includes a perimodiolar flexure 136 formed in a basal (proximal) section of the stimulating assembly (i.e., a section of the stimulating assembly 118 that is configured to be implanted in a basal region of the recipient's cochlea). In general, the perimodiolar flexure 136 is configured to (i.e., has elastic properties and a shape so as to), after insertion into the cochlea, position all of the stimulating contacts disposed in the basal section adjacent to a modiolar wall of the cochlea.

An intra-cochlear stimulating assembly, such as stimulating assembly 118, may be a perimodiolar stimulating assembly or a non-perimodiolar stimulating assembly. A perimodiolar stimulating assembly is a stimulating assembly that is configured to adopt a curved configuration during and/or after implantation into the recipient's cochlea so as to have a distal section positioned close to the wall of the recipient's modiolus (i.e., close to the modiolar wall). The modiolus is a conical shaped central region in the cochlea around which the cochlea canals (i.e., scala tympani, scala media, and scala vestibule) spiral. The modiolus consists of spongy bone in which the cochlea nerve cells, sometimes referred to herein as the spiral ganglion cells, are situated. The cochlea canals generally turn 2.5 times around the modiolus.

One type of non-perimodiolar stimulating assembly is a lateral stimulating assembly that is configured to be implanted adjacent to the lateral wall of the recipient's scala tympani (i.e., the wall that is opposite the modiolar wall). Another type of non-perimodiolar stimulating assembly is a mid-scala stimulating assembly which assumes a mid-scala position during or following implantation (i.e., positioned approximately midway between the modiolar wall and the lateral wall).

Figure 2:
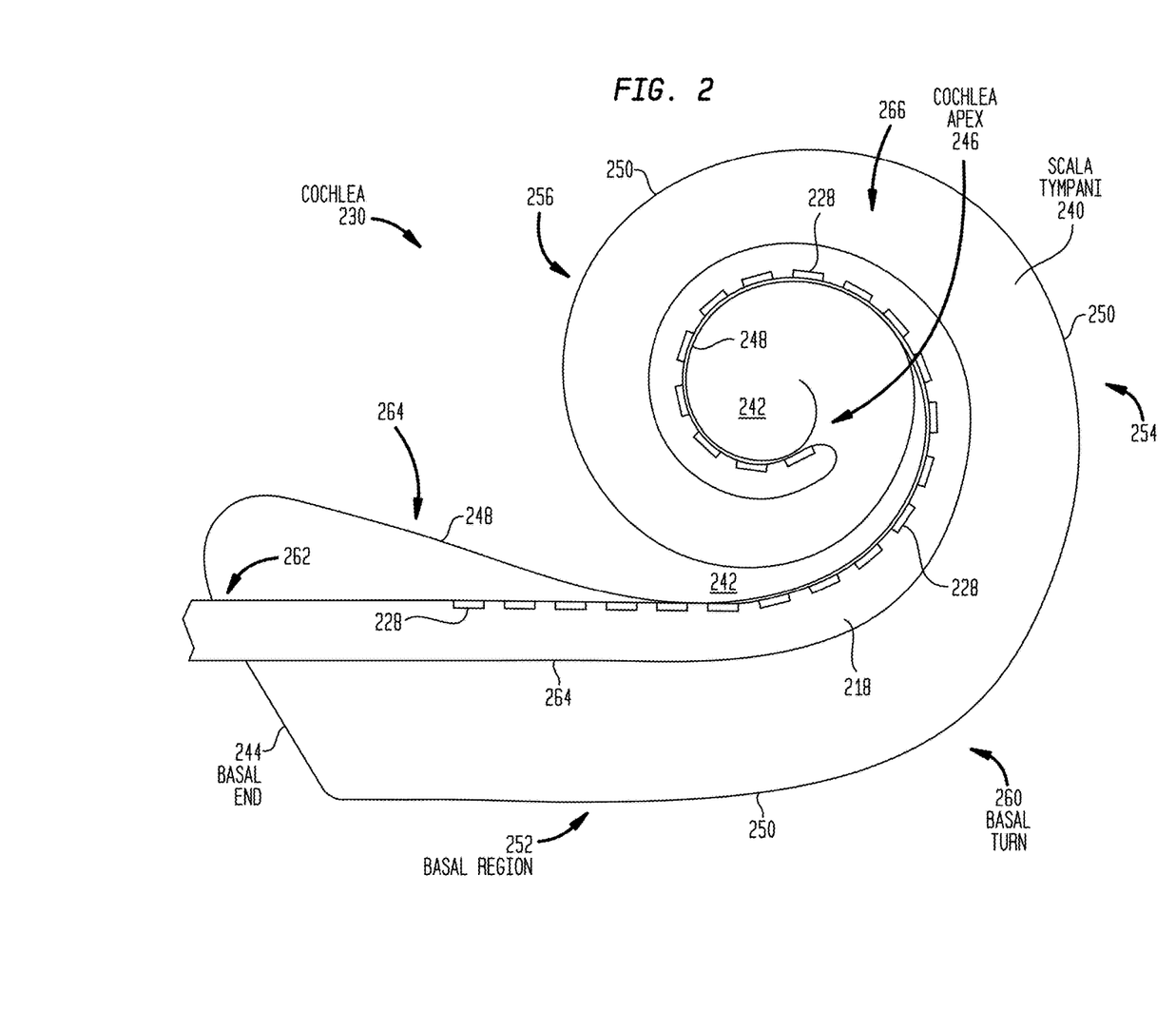
FIG. 2 is a schematic diagram of a partially perimodiolar stimulating assembly positioned in a recipient's cochlea.

FIG. 2 is a schematic diagram of a conventional perimodiolar stimulating assembly 218 implanted in the cochlea 230 of a recipient. The stimulating assembly 218 is shown implanted in a cochlea canal which, in this example, is the recipient's scala tympani 240. The scala tympani 240 generally spirals around the recipient's modiolus 242 and extends from a basal end/wall 244 to an apex 246. The scala tympani 240 includes a modiolar wall 248 and a lateral wall 250. The modiolar wall 248 is the wall of the scala tympani 240 that is adjacent to the modiolus 242 and the spiral ganglion cells (not shown). The lateral wall 250 is the wall of the scala tympani 240 that is opposite the modiolar wall 248 (i.e., spaced from the modiolus 242).

The cochlea 230 is generally divided into a basal region 252, a mid or middle region 254, and an apical region 256. The basal region 252 may be considered to be the region of the scala tympani 240 (or other cochlea canals) that extends between the basal end 244 to approximately the basal turn (first turn) 260. Since the basal region 252 terminates at the basal turn 260, the basal region 252 is generally straight.

The stimulating assembly 218 is typically inserted through an opening 262 (e.g., the round window or a cochleostomy) in the basal end 244 of the recipient's scala tympani 208. As shown, the stimulating assembly 218 includes a proximal (basal) section 264 that extends straight from the opening 262 and begins to turn at the basal turn 260. That is, the basal section 264 of the stimulating assembly 218 is generally straight.

The stimulating assembly 218 also includes a distal section 254 that extends from approximately the basal turn 260 to near the cochlea apex 246. In the distal section 254, the stimulating assembly 218 spirals around the modiolus 242 (i.e., as a curved arrangement).

The stimulating assembly 218 comprises a plurality of stimulating contacts 228. In the perimodiolar arrangement of FIG. 2, the stimulating contacts in the distal section 266 of the stimulating assembly 218 (i.e., the sections of the stimulating assembly configured to be implanted distal to the basal turn 260) are configured to be positioned adjacent to the modiolar wall 248. As such, the stimulating contacts 228 in the distal section 266 have a final implanted position close to (i.e., adjacent or abutting) the modiolar wall 248 and thus to the spiral ganglion cells. However, as shown in FIG. 2, in conventional arrangements the basal section 264 of the stimulating assembly 218, and thus the stimulating contacts 228 disposed in the basal section, is separated from the modiolar wall 248 (i.e., there are a number of contacts in the basal region and not close to the modiolar wall). This separation is due to the straight configuration of the basal section 264 and the natural curve 246 of the modiolar wall 248 in the basal region 252.

Figure 3A:
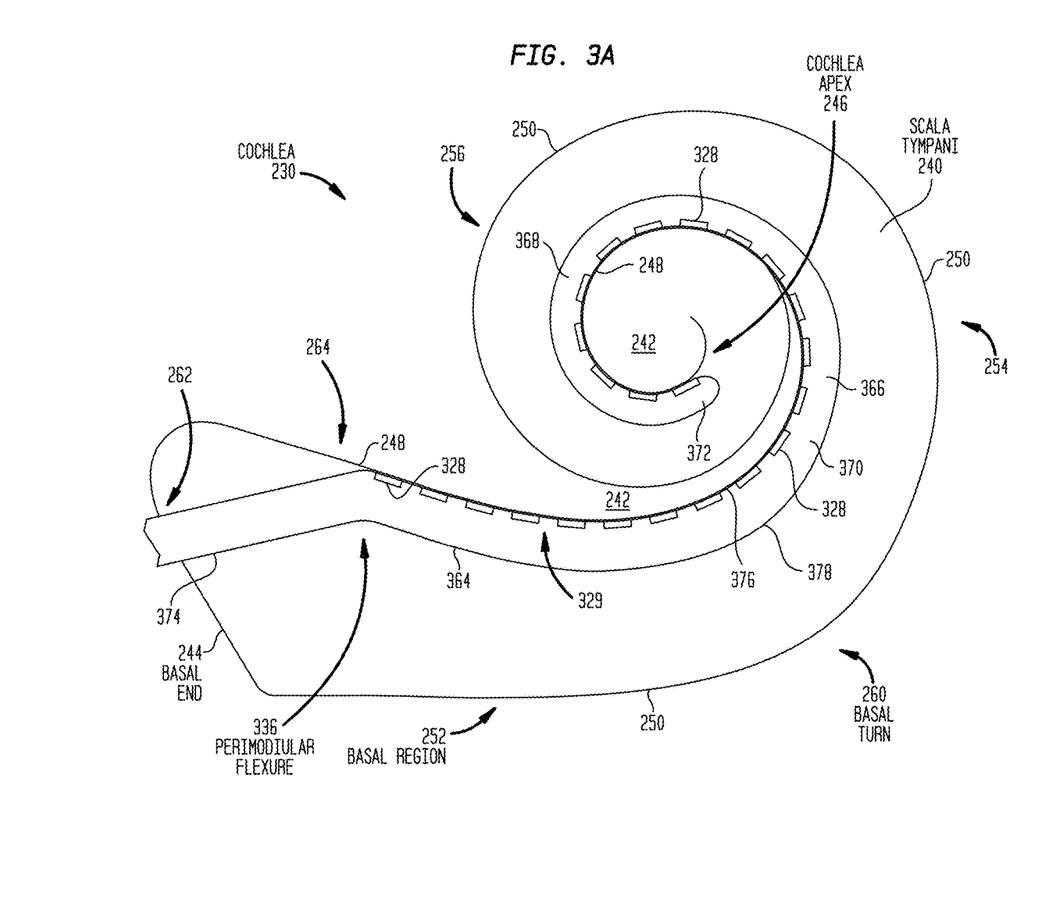
FIG. 3A is a schematic diagram of a fully perimodiolar stimulating assembly in accordance with embodiments presented herein shown positioned in a recipient's cochlea.

There may be a desire to have stimulating contacts in the basal section of a stimulating assembly positioned close to the modiolar wall, similar to the position of the more distal/apical stimulating contacts of a perimodiolar stimulating assembly. However, as illustrated above with reference to FIG. 2, the close positioning of a perimodiolar stimulating assembly to the basal end of the modiolar wall 248 is not possible with current stimulating assembly designs due to, for example, the straight entry of the stimulating assembly into the basal region, the straight basal section of the stimulating, assembly, etc. As such, FIG. 3A illustrates a stimulating assembly 318 in accordance with embodiments of the present invention where all of the stimulating contacts, including the stimulating contacts in the basal section of the stimulating assembly 318, can be positioned immediately adjacent to the modiolar wall of the cochlea. For ease of illustration, the stimulating assembly 318 is shown implanted in the cochlea 230 described above with reference to FIG. 2.

The stimulating assembly 318 is configured to be implanted in the scala tympani 240 via an opening 262. As noted above, the opening 262 may be a surgically formed opening (i.e., cochleostomy) or a natural opening (e.g., the round window). The stimulating assembly 318 comprises a carrier member 370 having a distal end (tip) 372 and a proximal end 374. Distal end 372 is adapted to be implanted furthest into the recipient's cochlea 230, while proximal end 374 is adapted to be positioned at opening 262. A plurality of spaced stimulating contacts 328 are mounted or disposed in/on at least a first surface 376 of the carrier member 370 between the proximal end 374 and the distal end 372. It should be appreciated that as used herein, particular combinations of the terms mounted/disposed, in/on, etc., are not to be interpreted to refer to any particular manufacturing technique or structural relationship.

The carrier member 370 includes a second surface 378 that opposes the first surface 376. The carrier member 370 may have, for example, a circular, oval, or other cross-sectional shape. As such, "opposing surfaces" refers to the fact that at least a portion of each of the surfaces 376 and 378 face in substantially opposing directions from one another. Carrier member 370 may be manufactured from a polymer material such as silicone and is connected to a lead region (not shown in FIG. 3A) from the proximal end 374. The lead region physically and electrically connects stimulating lead assembly 318 with a stimulator unit (not shown in FIG. 3A).

The stimulating assembly 318 may be generally referred to as including a proximal or basal section 364 and a distal section 366. The basal section 364 is the portion of the stimulating assembly 318 that, when implanted, is positioned within the basal region 252 of the cochlea 230 (i.e., the portion of the stimulating assembly that is proximal to the basal turn 260). The distal section 366 is generally the portion of the stimulating assembly 318 configured to be positioned past the basal turn 260 (i.e., the portion that extends from approximately the basal turn 260 to near the cochlea apex 246).

The basal section 364 may include approximately 4-8 stimulating contacts 328 that are individually and collectively referred to herein as basal region contacts 329 or simply basilar contacts 329. The basal section 364 of the stimulating assembly 318 also includes a pre-formed perimodiolar flexure 336 positioned adjacent to one or more of the basilar contacts 329. The perimodiolar flexure 336 is configured such that, when released to its pre-biased configuration, the perimodiolar flexure 336 forces the basilar contacts 329 into a position close to (i.e., adjacent to) the modiolar wall 248. In other words, the perimodiolar flexure 336 biases at least a portion of the basal section 364 towards the modiolar wall 248.

Figure 3B:
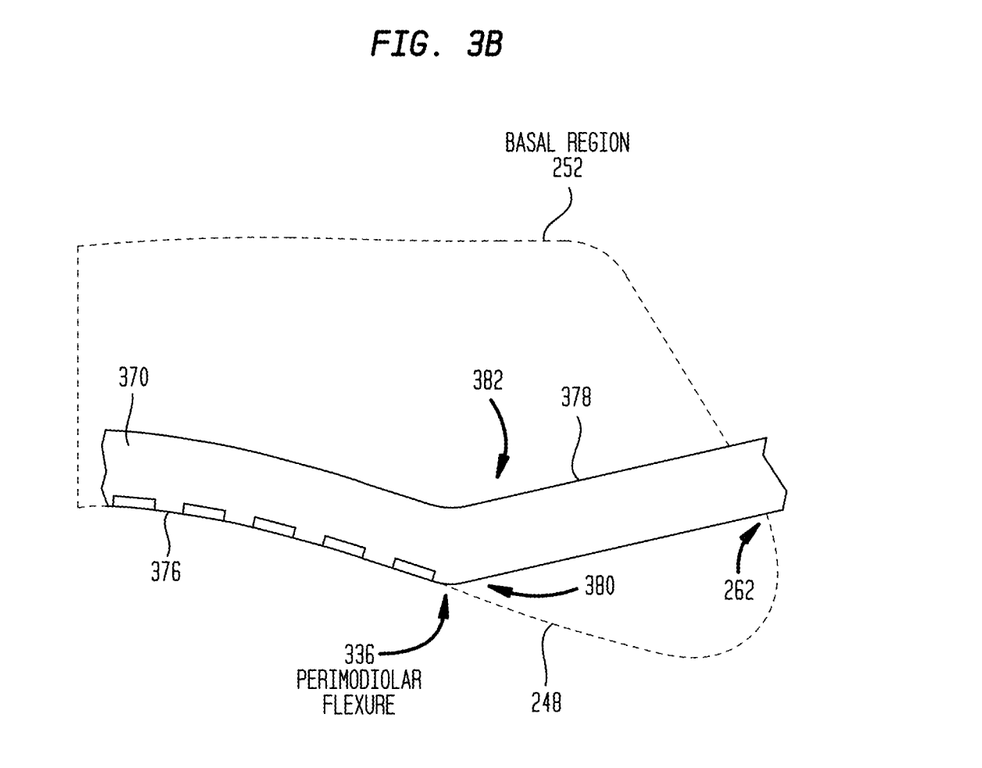
FIG. 3B is a schematic diagram of a perimodiolar flexure formed in the stimulating assembly of FIG. 3A.

FIG. 3B is a schematic diagram illustrating further details of the perimodiolar flexure 336. For ease of illustration, only a portion of the basal section 364 comprising the five (5) most proximal/basal basilar contacts 329 is shown in FIG. 3B. In general, all or subset of the five most proximal basilar contacts 329 are the contacts that are spaced from the modiolar wall 248 in conventional arrangements.

The perimodiolar flexure 336 is a pre-formed and pre-biased bend or kink in the direction of the modiolar wall 248. The perimodiolar flexure 336 forms a substantially smooth and continuous arcuate bend in the stimulating assembly 318 that, when implanted, opens towards the lateral wall 250 (i.e., an inverse curl to the predominate curl of the stimulating assembly 318 around the modiolus 242). At the perimodiolar flexure 336, the first surface 376 of the stimulating assembly 318 includes a convex curve 380 facing the modiolar wall 248, while the second surface 378 includes a concave curve 382 facing the lateral wall 250. As a result of the perimodiolar flexure 336, there is a significant trajectory change in the basal section 364 of the stimulating assembly 318 that generally form an obtuse angle.

As shown, the perimodiolar flexure 336 is positioned at (i.e., proximate to) one or more of the basilar contacts 329 and is separated from the proximal end 374 of the stimulating assembly 318. The shape and mechanical properties of the perimodiolar flexure 336 cause the portion of the first surface 376 in which the basilar contacts 329 are positioned to be adjacent to, or abut, the modiolar wall 248. As such, the perimodiolar flexure 336 enables the basilar contacts 329 to be in a perimodiolar position (i.e., positioned close to, or maintain contact with, the modiolar wall 248), which is not possible with conventional arrangements that have a straight basilar section. This closer position to the modiolar wall 248 puts the stimulating contacts closer to their target spiral ganglion cells, thereby possibly reducing the power requirements and potentially improving potential performance of the recipient by increasing the likelihood of stimulating the target spiral ganglion cells, rather than spiral ganglion cells further away (i.e., nerve cells that are not related to that target auditory frequency).

Stimulating assembly 318 shown in FIGS. 3A and 3B is sometimes referred to herein as "fully" or "completely" perimodiolar stimulating assembly because all of the stimulating contacts, including those in the basal section of the stimulating assembly, have a perimodiolar position (i.e., are close to or abutting the modiolar wall). As noted above, conventional stimulating assemblies are not fully/completely perimodiolar stimulating assemblies due to the use of straight basilar sections in which the basilar contacts are separated from the modiolar wall.

Figure 4:
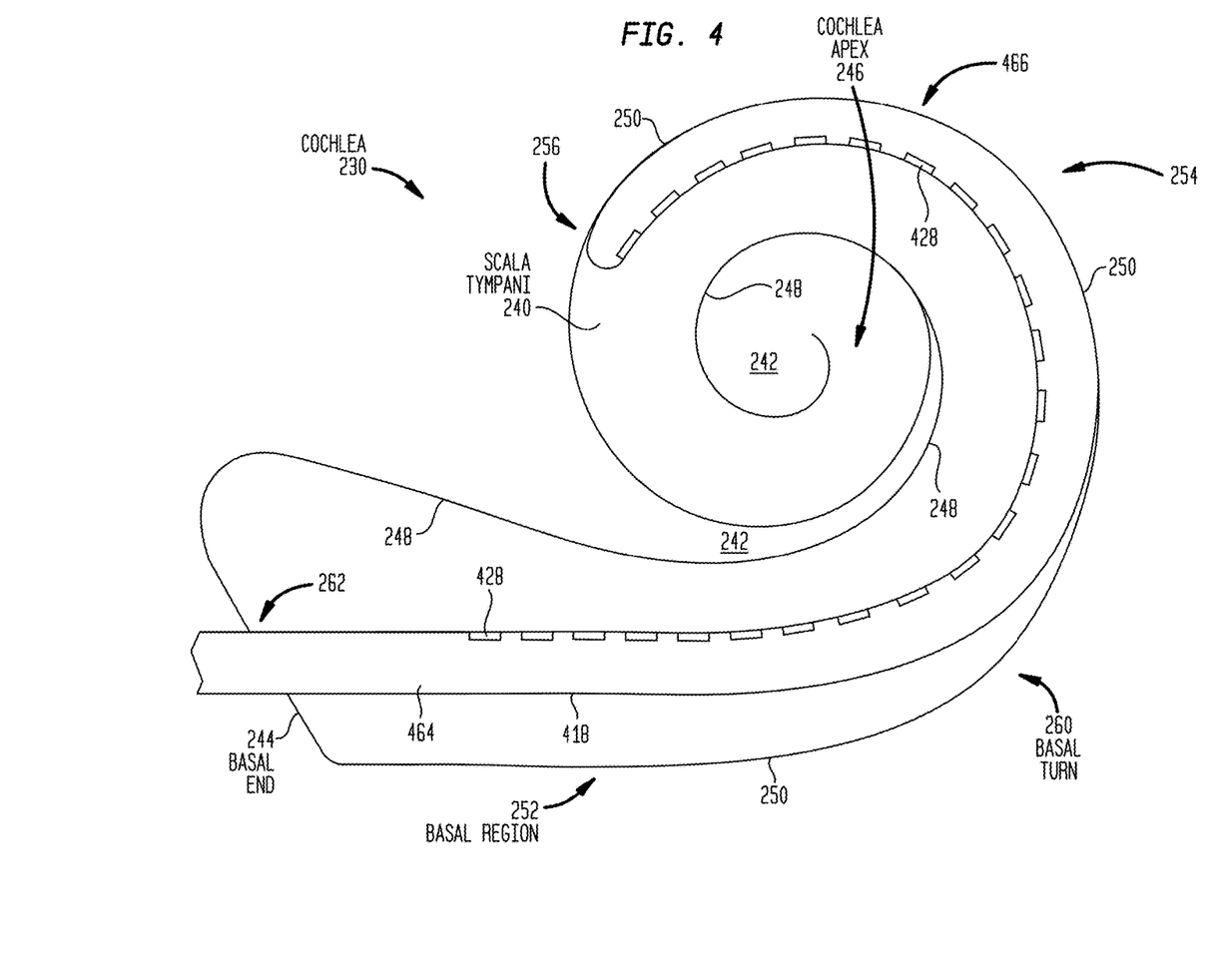
FIG. 4 is a schematic diagram of a lateral stimulating assembly positioned in a recipient's cochlea.
Figure 5:
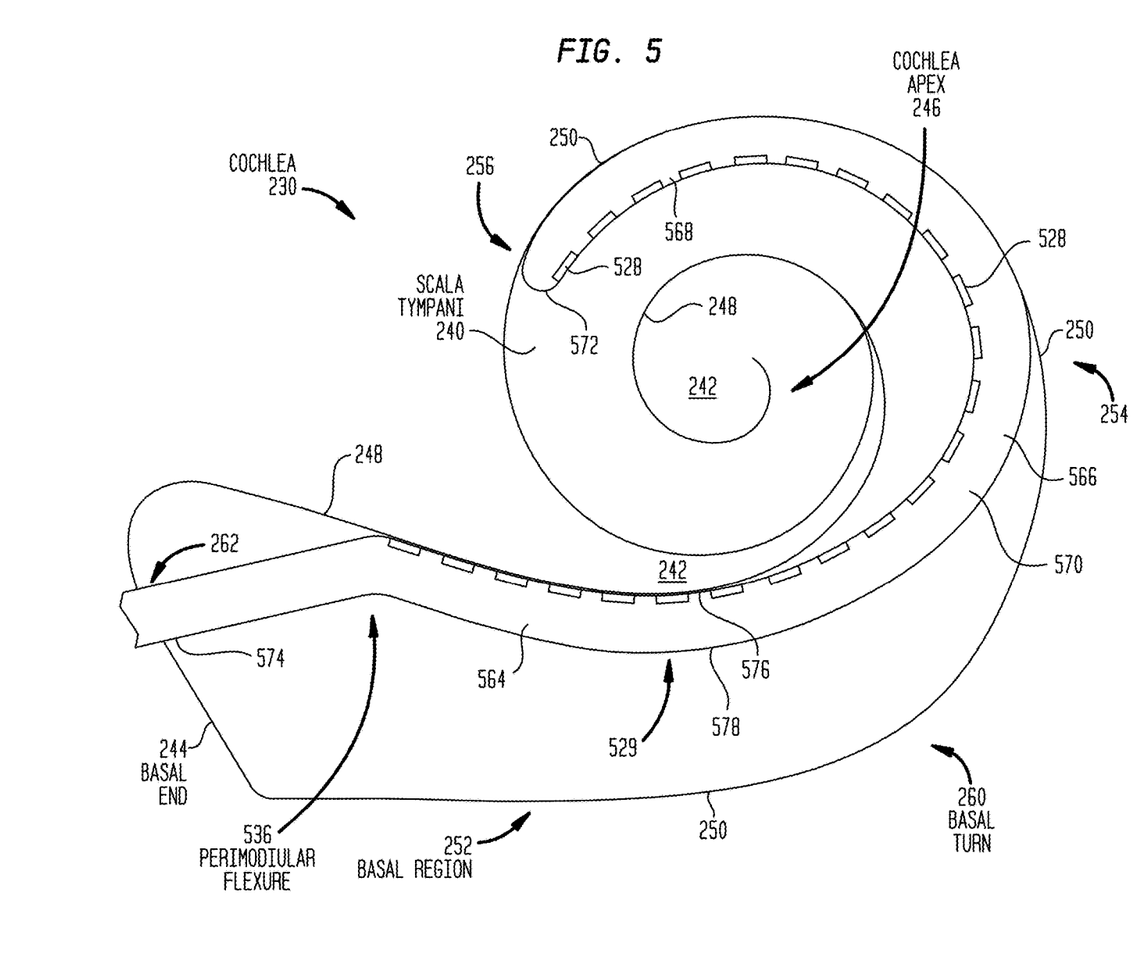
FIG. 5 is a schematic diagram of a combined perimodiolar-lateral stimulating assembly in accordance with embodiments presented herein shown positioned in a recipient's cochlea.

As noted above, a stimulating assembly can be a perimodiolar stimulating assembly or a non-perimodiolar stimulating assembly (e.g., a lateral stimulating assembly or a mid-scala stimulating assembly). FIG. 4 illustrates a conventional lateral stimulating assembly, while FIG. 5 illustrates a lateral stimulating assembly that includes a perimodiolar flexure in accordance with embodiments of the present invention. For ease of illustration, the stimulating assemblies of FIGS. 4 and 5 are described and shown implanted in the cochlea 230 of FIG. 2.

Referring first to FIG. 4, a stimulating assembly 418 is inserted through the opening 262 and includes a proximal (basal) section 464 and a distal section 466. The basal section 464 extends straight from the opening 262 and to the basal turn 260. That is, the basal section 464 of the stimulating assembly 218 is generally straight. The stimulating assembly 418 begins to turn at the basal turn 260 (and the end of the basal section 464) such that the distal section 466 spirals around the modiolus 242 along the lateral wall 250.

The stimulating assembly 418 comprises a plurality of stimulating contacts 428. In the lateral arrangement of FIG. 4, all of the stimulating contacts 428 are spaced from the modiolar wall 248 (i.e., the stimulating assembly 428 follows the lateral wall 250).

FIG. 5 illustrates a stimulating assembly design that uses a perimodiolar flexure to enable a combination of aspects of a perimodiolar stimulating assembly (as described with reference to FIGS. 3A and 3B) with a lateral stimulating assembly. More specifically, FIG. 5 illustrates a stimulating assembly 518 that is configured to be implanted in the scala tympani 240 via opening 262. The stimulating assembly 518 comprises a carrier member 570 having a distal end (tip) 572 and a proximal end 574. Distal end 572 is adapted to be implanted furthest into the recipient's cochlea 230, while proximal end 574 is adapted to be positioned at opening 262. A plurality of spaced stimulating contacts 528 are mounted or disposed in/on at least a first surface 576 of the carrier member 570 between the proximal end 574 and the distal end 572.

The carrier member 570 includes a second surface 578 that generally opposes the first surface 576. Carrier member 570 may be manufactured from a polymer material such as silicone and is connected to a lead region (not shown in FIG. 5) from the proximal end 574. The lead region physically and electrically connects stimulating lead assembly 518 with a stimulator unit (also not shown in FIG. 5).

The stimulating assembly 518 may be generally referred to as including a proximal (basal) section 564 and a distal section 566. The basal section 564 is the portion of the stimulating assembly 518 that, when implanted, is positioned within the basal region 252 of the cochlea 230 (i.e., the portion of the stimulating assembly that is proximal to the basal turn 260). The distal section 566 is generally the portion of the stimulating assembly 518 configured to be positioned past the basal turn 260 (i.e., the portion that extends from approximately the basal turn 260 to near the cochlea apex 246).

The basal section 564 may include approximately 4-8 stimulating contacts 328 that are individually and collectively referred to herein as basal region contacts 529 or simply basilar contacts 529. The basal section 564 of the stimulating assembly 518 also includes a pre-formed perimodiolar flexure 536 positioned adjacent to one or more of the basilar contacts 529. The perimodiolar flexure 536 is configured such that, when released to its pre-biased configuration, the perimodiolar flexure 536 forces the basilar contacts 529 into a position close to (i.e., adjacent to) the modiolar wall 248. In other words, the perimodiolar flexure 536 biases at least a portion of the basal section 564 towards the modiolar wall 248.

The perimodiolar flexure 536 is a pre-formed and pre-biased bend or kink in the direction of the modiolar wall 248. The perimodiolar flexure 536 forms a substantially smooth and continuous arcuate bend in the stimulating assembly 518 that, when implanted, opens towards the lateral wall 250 (i.e., an inverse curl to the predominate curl of the stimulating assembly 518 around the modiolus 242). At the perimodiolar flexure 536, the first surface 576 of the stimulating assembly 518 includes a convex curve 580 facing the modiolar wall 248, while the second surface 578 includes a concave curve 582 facing the lateral wall 250. As a result of the perimodiolar flexure 536, there is a significant trajectory change in the basal section 564 the stimulating assembly 518 that generally form an obtuse angle.

As shown, the perimodiolar flexure 536 is positioned at (i.e., proximate to) one or more of the basilar contacts 529 and is separated from the proximal end 574 of the stimulating assembly 518. The shape and mechanical properties of the perimodiolar flexure 536 cause the portion of the first surface 576 in which the basilar contacts 329 are positioned to be adjacent to, or abut, the modiolar wall 248. As such, the perimodiolar flexure 336 enables the basilar contacts 529 to be in a perimodiolar position (i.e., positioned close to, or maintain contact with, the modiolar wall 248), which is not possible with conventional arrangements that have a straight basilar section.

Due to the presence of the perimodiolar flexure 536, the basal section 564 of the stimulating assembly 518 is configured to adopt a perimodiolar position. However, the remainder of the stimulating assembly 518 is configured to adopt a lateral position (i.e., only the basal section of stimulating assembly 518 has a perimodiolar arrangement). More specifically, a first part of the proximal section 564 of the stimulating assembly 518, namely a portion extending through mid region 254 of the cochlea 230, functions as a "transition region" for the stimulating assembly 518. That is, the first part of the distal 566 is the region in which the stimulating assembly 518 switches from a perimodiolar position to a lateral position. The stimulating assembly 518 shown in FIG. 5 is sometimes referred to herein as a combined perimodiolar-lateral stimulating assembly.

The combined perimodiolar-lateral stimulating assembly arrangement of FIG. 5 may be useful so as to combine the low trauma/hearing preservation nature of a lateral electrode insertion (i.e., insertion away from the modiolar wall that could damage spiral ganglion cells), with a formed basal section to closely position stimulating contacts in the high frequency range of the cochlea. In general, the high frequency range, which correlates to the basal region of the cochlea, encompasses the frequencies that are no longer functional in patients who have only residual low frequency hearing and, as such, are candidates for hybrid cochlear implants or other auditory prosthesis that delivery acoustic/mechanical stimulation.

It is to be appreciated that the specific stimulating assemblies of FIGS. 3A, 3B, and 5 are illustrative and variations to these or other stimulating assemblies are within the scope of the embodiments presented herein. For example, stimulating assemblies in accordance with other embodiments may include different numbers of stimulating contacts, have different lengths (e.g., short stimulating assemblies), etc.

As noted above, stimulating assemblies in accordance with embodiments of the present invention include a perimodiolar flexure formed in the basal section that has elastic properties and a shape so as to, after insertion into the cochlea, position all of the stimulating contacts disposed in the basal section adjacent to a modiolar wall of the cochlea. In certain embodiments, a perimodiolar flexure may be introduced through a specific configuration of the stimulating assembly carrier member. That is, the perimodiolar flexure may be introduced by molding the basal section of the carrier member to include the perimodiolar flexure shape (i.e., forming the silicone carrier member with the pre-biased bend).

As noted above, a carrier member may be formed from a resiliently flexible polymer material, such as silicone. In embodiments in which the carrier member is formed into the perimodiolar flexure shape, the carrier member would be straightened using, for example, a stiffening member (e.g., a removable stylet within the carrier member, a permanent temperature-responsive stiffener, outer stiffening sheath, etc.) during insertion. That is, the stiffening member would maintain the perimodiolar flexure in a generally straight configuration for the initial insertion. During or after insertion, the stiffening member may be removed/deactivated so as to "release" the perimodiolar flexure into its pre-formed (arcuate bend) configuration. That is, due to the elastic properties of the resiliently flexible polymer material and the pre-formed shape, the perimodiolar flexure will form the arcuate bend when released from the straight configuration.

In other embodiments, the perimodiolar flexure may be introduced through the use of a forming/shaping member disposed within the carrier member. In one specific example, the shaping member is a permanent superelastic member that may be useful to reduce the cross-section of the stimulating assembly by reducing the bulk silicone as well as producing a more repeatable pre-curved shape.

Figure 6A:
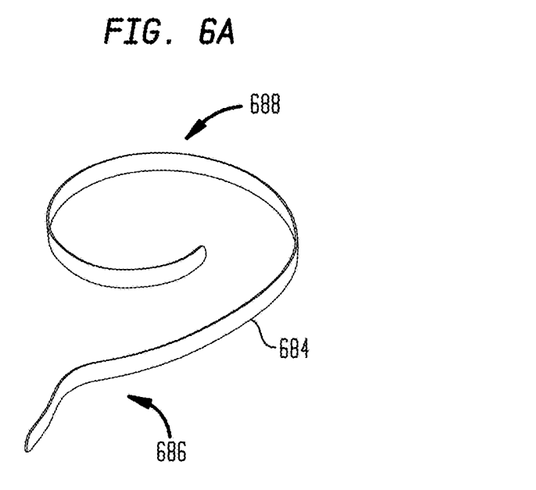
FIG. 6A is a perspective view of a superelastic forming member in accordance with embodiments presented herein.

More specifically, FIG. 6A is a perspective view of a superelastic member 684 that may be used to form a perimodiolar flexure in accordance with embodiments of the present invention. The superelastic shaping member 684 includes a proximal section 686 that is pre-formed into the shape of the perimodiolar flexure. The superelastic shaping member 684 also comprises a distal section 688 that is generally curled to follow the spiral of the modiolus. In general, the curl of the distal section 688 creates a tight, repeatable perimodiolar position of the distal section of a stimulating assembly.

Superelasticity, sometimes referred to as pseudoelasticity, is an elastic response to an applied stress, induced by a phase transformation between the phases (e.g., austenitic and martensitic) of a crystal. A superelastic (pseudoelastic) material is configured to return to its original (pre-formed) shape after the removal of even relatively high applied strains. When mechanically loaded, a superelastic material is placed in a stress-induced phase. When the load is removed, the new phase becomes unstable and the material regains its original shape. Unlike shape-memory alloys, no change in temperature is needed for the alloy to recover its initial shape. As such, the superelastic shaping member 684 takes advantage of the large and reversible deformation so as to return to the pre-formed shape (i.e., curled distal section and an arcuate bend in the proximal section) when released from the straight configuration (i.e., that applies a strain to the superelastic shaping member 684). Nickel/titanium alloys are examples of superelastic materials. As such, in one specific embodiment, the superelastic shaping member 684 is formed from a Nickel/titanium alloy that does not change its configuration/properties based on temperature (i.e., a non-temperature responsive Nickel/titanium alloy).

Figure 6B:
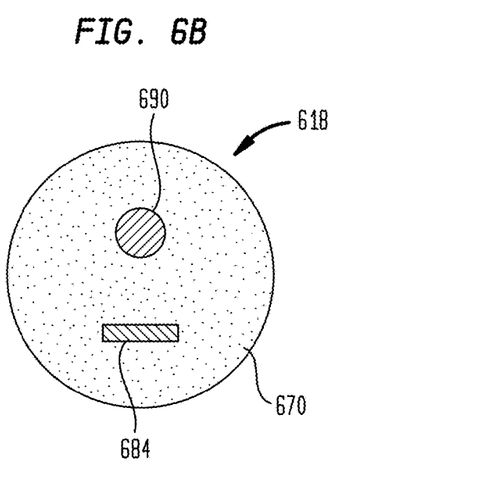
FIG. 6B is lateral cross-sectional view of a stimulating assembly that includes the superelastic forming member of FIG. 6A.
Figure 6C:
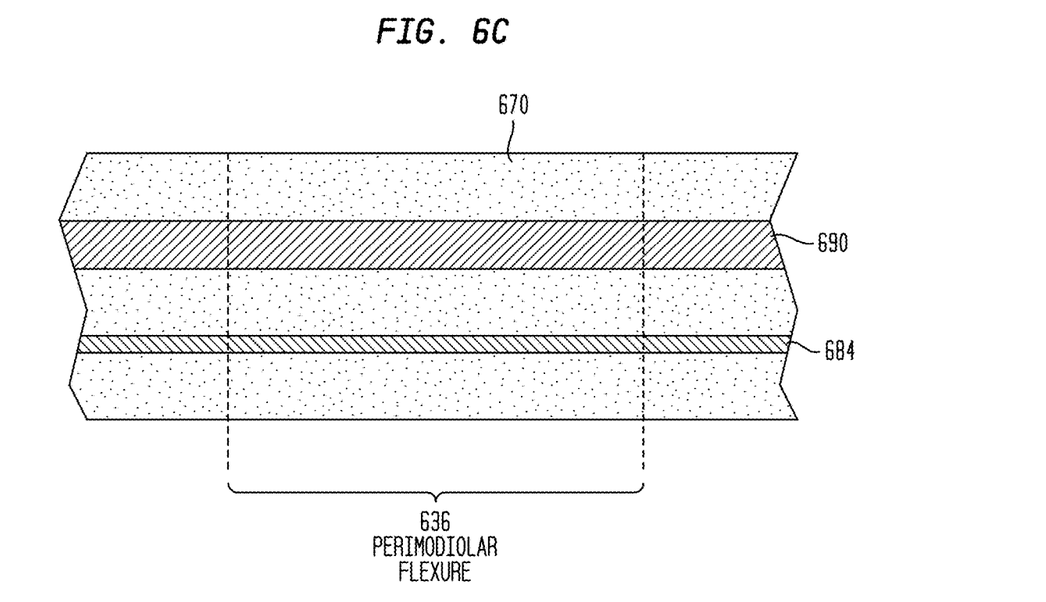
FIG. 6C is a longitudinal cross-sectional view of a portion stimulating assembly that includes the superelastic forming member of FIG. 6A.
Figure 6D:
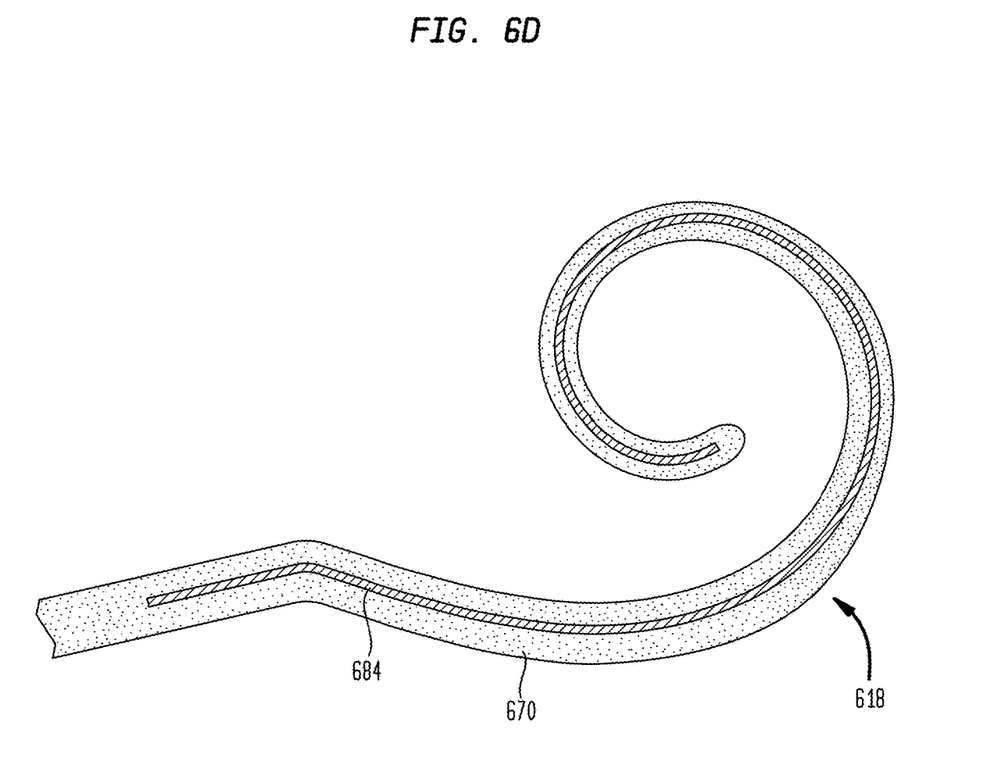
FIG. 6D is another longitudinal cross-sectional view of a stimulating assembly that includes the superelastic forming member of FIG. 6A.

FIG. 6B is a lateral cross-sectional view of a stimulating assembly 618 in which the superelastic shaping member 684 of FIG. 6A is positioned. FIG. 6C is a longitudinal cross-sectional view of a portion of the stimulating assembly 618. FIG. 6D is another longitudinal cross-sectional view illustrating the stimulating assembly 618 in its implanted configuration. For ease of illustration, the stimulating contacts and lead wires have been omitted from FIGS. 6B-6D.

As shown in FIGS. 6B and 6C, the stimulating assembly 618 comprises a carrier member 670. Embedded in the carrier member 670 is the superelastic shaping member 684 and a removable stiffening stylet 690. The stiffening stylet 690 is configured to straighten the carrier member 670 during insertion. That is, the stiffening stylet 690 has sufficient strength to maintain the superelastic shaping member 684, and the perimodiolar flexure 636, in a straight configuration during insertion. During or after insertion, the stiffening stylet 690 is removed so as to "release" the superelastic shaping member 684. After release, the perimodiolar flexure 636 returns to the pre-formed (arcuate bend) configuration. That is, due to the superelastic properties of the superelastic shaping member and the pre-formed shape, the perimodiolar flexure 636 will form the arcuate bend when released from the straight configuration. FIG. 6D is another longitudinal cross-sectional view illustrating the stimulating assembly 618 in its implanted configuration (i.e., the shape that the stimulating assembly resumes after the stiffening stylet 690 is removed).

Figure 7:
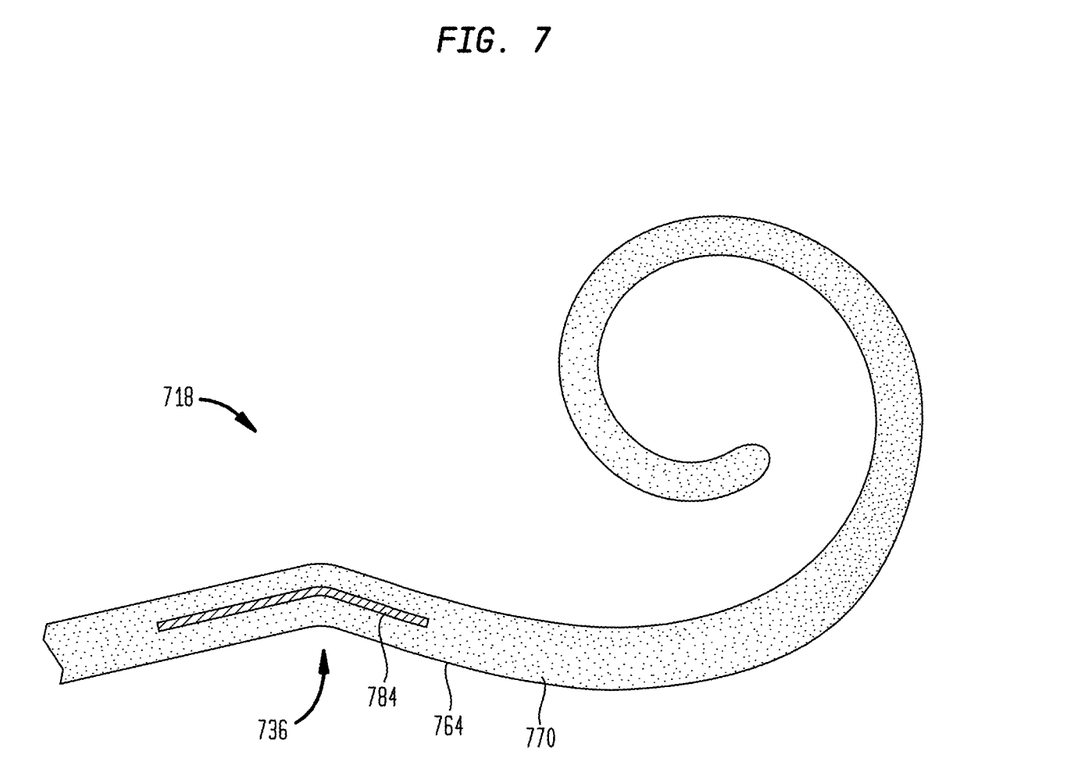
FIG. 7 is a longitudinal cross-sectional view of a stimulating assembly that includes another superelastic forming member in accordance with embodiments presented herein.

FIGS. 6A-6C illustrate the use of a shaping member that extends through a substantial portion of the carrier member. However, it is to be appreciated that a shaping member may extend through only smaller selective sections of a carrier member. For example, FIG. 7 illustrates a stimulating assembly 718 having a shaping member 784 that extends through only a basal section 764 of the carrier member 770 so as to straighten a perimodiolar flexure 736. Such an arrangement may be used, for example, with a combined perimodiolar-lateral stimulating assembly. For ease of illustration, the stimulating contacts and lead wires have been omitted from FIG. 7.

Figure 8A:
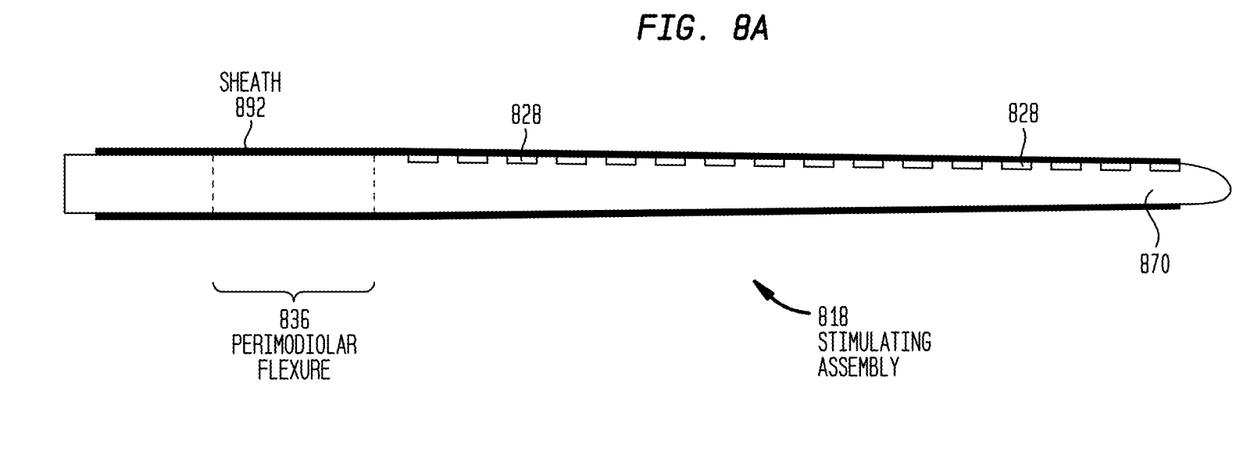
FIG. 8A is a side view of a stimulating assembly that includes a perimodiolar flexure held in a straight configuration through the use of a stiffening sheath in accordance with embodiments presented herein.
Figure 8B:
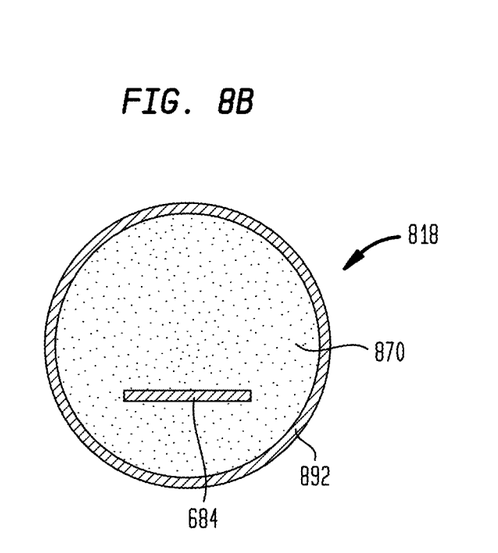
FIG. 8B is lateral cross-sectional view of the stimulating assembly of FIG. 8A.
Figure 8C:
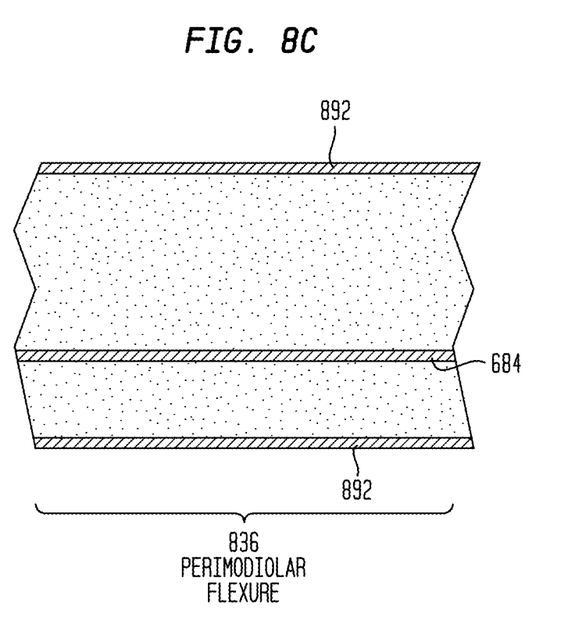
FIG. 8C is a longitudinal cross-sectional view of a portion of the stimulating assembly of FIG. 8A.

FIGS. 6B and 6C also illustrated the specific use of a stiffening stylet to retain the perimodiolar flexure in a straight arrangement for insertion into the cochlea. FIGS. 8A-8C illustrate an alternative arrangement for a stimulating assembly that uses a stiffening sheath 892 rather than an embedded stiffening stylet. More specifically, FIG. 8A is side-view of a stimulating assembly 818, FIG. 8B is a lateral cross-sectional view of the stimulating assembly 818, and FIG. 8C is a longitudinal cross-sectional view of a portion of the stimulating assembly 818.

As shown, the stimulating assembly 818 comprises a plurality of stimulating contacts 828 (FIG. 8A) disposed in a carrier member 870. Also embedded in the carrier member is the superelastic shaping member 684 of FIG. 6A. The stiffening sheath 892 is disposed around an outer surface of the carrier member 870 and is configured to straighten the carrier member 870 during insertion into a recipient's cochlea. That is, the stiffening sheath 892 has sufficient strength to maintain the superelastic shaping member 684, and the perimodiolar flexure 836, in a straight configuration during insertion. During or after insertion, the stiffening sheath 892 is removed so as to "release" the superelastic shaping member 684. After release, the perimodiolar flexure 836 returns to the pre-formed (arcuate bend) configuration. That is, due to the superelastic properties of the superelastic shaping member and the pre-formed shape, the perimodiolar flexure 836 will form the arcuate bend when released from the straight configuration.

There are several options available to manufacture a stimulating assembly to include a superelastic shaping member in accordance with embodiments presented herein. In on example, the carrier member could be molded into a curled state after a typical straight molding process (i.e., a secondary mold to form a curled configuration). In such examples, in place of a stylet to form a lumen, the pre-formed superelastic shaping member would be overmolded and left in place within the carrier member.

In an alternative example, the stimulating contacts and lead wires can be initially assembled in a straight configuration. Additionally, the pre-curved superelastic shaping member can be temporarily straightened and positioned within a molding die on top of the stimulating contacts and lead wires. A resiliently flexible polymer material, such as silicone, may then be injected into the molding die to encapsulate the contacts, lead wires, and the superelastic shaping member, thereby forming a single assembly. When removed from the molding die, the stimulating assembly is operable to spring back to the shape of the pre-curved superelastic shaping member, effectively creating a perimodiolar electrode using straight electrode manufacturing techniques (i.e., an advantage to use of a superelastic shaping member is that the need to manufacture the stimulating assembly in a curved configuration is removed). In certain embodiments, a lumen for a stiffening element may also be formed during the molding process and/or a stiffening element may be molded into the assembly.

The manufacturing process described above may be arranged such that, during the straightening of the superelastic shaping member, no material stress is placed on the superelastic shaping member that is beyond its yield strength. This ensures that the superelastic shaping member will "spring" back to its pre-formed shape (i.e., ensuring that the superelastic shaping member operates only within the elastic region of the stress-strain curve). The peak stress that is induced in the material may be characterized by the bending moment induced at a specific location along the curly profile (which in turn is defined by radius of curvature at this point), and the thickness of the material at this position, with the highest stresses recorded at the distance furthest from the neutral axis.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A stimulating assembly for insertion into a cochlea of a recipient through an opening in the cochlea, comprising:
   an elongate carrier member having a basal section configured to be implanted in a basal region of the recipient's cochlea;
   a plurality of stimulating contacts disposed along at least a first surface of the carrier member, wherein a subset of the stimulating contacts are disposed in the basal section; and
   a perimodiolar flexure comprising a portion of the basal section of the elongate carrier member that is pre-molded into a pre-biased arcuate bend shape configured to, after insertion into the cochlea, position all of the stimulating contacts disposed in the basal section adjacent to a modiolar wall of the cochlea.

2. The stimulating assembly of claim 1, wherein, during insertion through an opening in the cochlea, the perimodiolar flexure has a straight configuration and is configured to adopt the pre-biased arcuate bend shape only after insertion through the opening in the cochlea.

3. The stimulating assembly of claim 1, further comprising:
   a shaping member permanently disposed in the portion of the basal section of the elongate carrier member that is pre-molded into the pre-biased arcuate bend shape.

4. The stimulating assembly of claim 3, wherein the shaping member is formed from a superelastic Nickel/titanium alloy.

5. The stimulating assembly of claim 1, wherein a distal section of the stimulating assembly is configured to adopt a perimodiolar position such that the stimulating assembly forms a fully perimodiolar stimulating assembly.

6. The stimulating assembly of claim 1, wherein a distal section of the stimulating assembly is configured to adopt a lateral position such that the stimulating assembly forms a combined perimodiolar-lateral stimulating assembly.

7. The stimulating assembly of claim 1, wherein the perimodiolar flexure is located adjacent to only the stimulating contacts in the basal section.

8. The stimulating assembly of claim 7, further comprising a portion of the basal section of the elongate carrier member that is pre-molded into a pre-biased arcuate bend shape.

9. An apparatus, comprising:
   an elongate carrier member having a proximal section and a distal section implantable in a recipient's cochlea; and
   a plurality of stimulating contacts disposed in the carrier member,
   wherein a first portion of the proximal section of the carrier member is pre-molded into an arcuate bend shape where a first surface of the first portion of the proximal section that faces a modiolar wall of the cochlea is formed into a convex curve and a second opposing surface of the first portion of the proximal section that faces a lateral wall of the cochlea is formed into a concave curve.

10. The apparatus of claim 9, wherein during insertion through an opening in the cochlea, the first portion of the proximal section of the carrier member has a straight configuration and, wherein the first portion of the proximal section of the carrier member forms the arcuate bend shape only after insertion through the opening in the cochlea.

11. The apparatus of claim 9, wherein a shaping member is permanently disposed in the carrier member, and wherein a section of the shaping member within the first portion of the proximal section is formed into an arcuate bend.

12. The apparatus of claim 11, wherein the shaping member is formed from a superelastic Nickel/titanium alloy.

13. The apparatus of claim 9, wherein the arcuate bend is configured to, after insertion into the cochlea, exert a bias force on the carrier member to position all of the stimulating contacts disposed in the proximal section adjacent to the modiolar wall of the cochlea.

14. The apparatus of claim 9, wherein the distal section of the carrier member is configured to adopt a perimodiolar position when implanted into the cochlea.

15. The apparatus of claim 9, wherein the distal section of the carrier member is configured to adopt a lateral position when implanted into the cochlea.

16. The apparatus of claim 9, wherein the arcuate bend is positioned adjacent to only stimulating contacts in the proximal section.

17. A stimulating assembly for insertion into a cochlea of a recipient through an opening in the cochlea, comprising:

an elongate carrier member having a basal section configured to be implanted in a basal region of the recipient's cochlea;

a plurality of stimulating contacts disposed along at least a first surface of the carrier member, wherein a subset of the stimulating contacts are disposed in the basal section; and a perimodiolar flexure comprising a segment of a shaping member permanently disposed in the basal section of the elongate carrier member, wherein the segment forms an arcuate bend shape.

18. The stimulating assembly of claim 17, wherein the perimodiolar flexure is located adjacent to only the stimulating contacts in the basal section.

19. The stimulating assembly of claim 17, wherein, during insertion through an opening in the cochlea, the perimodiolar flexure has a straight configuration and is configured to adopt the pre-biased arcuate bend shape only after insertion through the opening in the cochlea.

20. The stimulating assembly of claim 17, wherein the shaping member is formed from a superelastic Nickel/titanium alloy.

* * * * *